United States Patent
Yoshino et al.

(10) Patent No.: US 10,538,732 B2
(45) Date of Patent: Jan. 21, 2020

(54) CELL ISOLATION METHOD AND CELL TRAPPING FILTER

(71) Applicant: National University Corporation Tokyo University of Agriculture and Technology, Tokyo (JP)

(72) Inventors: Tomoko Yoshino, Tokyo (JP); Tsuyoshi Tanaka, Tokyo (JP); Tadashi Matsunaga, Tokyo (JP); Ryo Negishi, Tokyo (JP); Hisashige Kanbara, Tokyo (JP); Seita Nakamura, Tokyo (JP)

(73) Assignee: National University Corporation Tokyo University of Agriculture and Technology, Tokyo (JP)

( * ) Notice: Subject to any disclaimer, the term of this patent is extended or adjusted under 35 U.S.C. 154(b) by 29 days.

(21) Appl. No.: 15/523,237

(22) PCT Filed: Oct. 29, 2015

(86) PCT No.: PCT/JP2015/080588
§ 371 (c)(1),
(2) Date: Apr. 28, 2017

(87) PCT Pub. No.: WO2016/068249
PCT Pub. Date: May 6, 2016

(65) Prior Publication Data
US 2017/0321183 A1    Nov. 9, 2017

(30) Foreign Application Priority Data
Oct. 31, 2014    (JP) ................. 2014-223110

(51) Int. Cl.
*C12M 1/00*    (2006.01)
*C12M 1/12*    (2006.01)
(Continued)

(52) U.S. Cl.
CPC .............. *C12M 47/04* (2013.01); *C12M 1/12* (2013.01); *C12M 1/28* (2013.01); *C12M 3/06* (2013.01);
(Continued)

(58) Field of Classification Search
None
See application file for complete search history.

(56) References Cited

U.S. PATENT DOCUMENTS

2008/0227203 A1*   9/2008   Watanabe ............. C08F 220/56
                                          435/402
2009/0117656 A1*   5/2009   Akashi .................... A61L 27/52
                                          435/397
(Continued)

FOREIGN PATENT DOCUMENTS

EP    2363501 A1    9/2011
GB    2175312 A    11/1986
(Continued)

OTHER PUBLICATIONS

Baker et al., Cell Trans., 6(6):585-595 (1997) (Year: 1997).*
(Continued)

*Primary Examiner* — Thomas J. Visone
(74) *Attorney, Agent, or Firm* — Morgan, Lewis & Bockius LLP (57) ABSTRACT

A cell isolation method includes: a cell trapping step of allowing a test liquid to pass through a cell trapping filter which has a plurality of through-holes in the thickness direction, thereby trapping isolation target cells contained in the test liquid on one surface of the cell trapping filter; a gel embedding step of introducing a stimulus-responsive hydrogel onto the one surface of the cell trapping filter on which the cells have been trapped in the cell trapping step, thereby embedding the cells in the stimulus-responsive hydrogel; a
(Continued)

gel hardening step of applying a stimulus to the stimulus-responsive hydrogel in which the cells are embedded, thereby hardening the stimulus-responsive hydrogel; and a detachment step of detaching the stimulus-responsive hydrogel that was hardened in the gel hardening step from the cell trapping filter.

14 Claims, 8 Drawing Sheets

(51) Int. Cl.
*C12M 3/06* (2006.01)
*C12N 1/02* (2006.01)
*C12M 1/28* (2006.01)
*C12M 1/26* (2006.01)
*G01N 1/40* (2006.01)

(52) U.S. Cl.
CPC .............. *C12M 33/14* (2013.01); *C12N 1/02* (2013.01); *G01N 2001/4088* (2013.01)

(56) References Cited

U.S. PATENT DOCUMENTS

| | | | |
|---|---|---|---|
| 2009/0123544 A1* | 5/2009 | Liu | A61K 9/06 514/1.1 |
| 2011/0053152 A1 | 3/2011 | Goldkorn et al. | |
| 2011/0313066 A1* | 12/2011 | Jaber | C07K 1/30 521/31 |
| 2012/0183946 A1* | 7/2012 | Tang | A61M 1/34 435/2 |
| 2012/0208255 A1* | 8/2012 | Andersen | C12M 33/14 435/178 |
| 2012/0270209 A1* | 10/2012 | Shah | C12N 11/04 435/6.1 |
| 2013/0059288 A1* | 3/2013 | Dankbar | C12Q 1/6806 435/2 |
| 2017/0176428 A1* | 6/2017 | Kevlahan | G01N 33/54353 |

FOREIGN PATENT DOCUMENTS

| | | |
|---|---|---|
| JP | S62-006690 A | 1/1987 |
| JP | H09-145571 A | 6/1997 |
| JP | 2000-266744 A | 9/2000 |
| JP | 2005-102628 A | 4/2005 |
| JP | 2005-261339 A | 9/2005 |
| JP | 2008-043782 A | 2/2008 |
| JP | 2008-507293 A | 3/2008 |
| JP | 2010-518812 A | 6/2010 |
| JP | 2012-092137 A | 5/2012 |
| JP | 2014-508516 A | 4/2014 |
| JP | 2015-188323 A | 11/2015 |
| WO | 2004/041994 A1 | 5/2004 |
| WO | 2006/011854 A1 | 2/2006 |
| WO | 2008/100497 A1 | 8/2008 |
| WO | 2010/135603 A2 | 11/2010 |
| WO | 2012/103516 A1 | 8/2012 |
| WO | 2013/036819 A1 | 3/2013 |
| WO | 2013/172265 A1 | 11/2013 |
| WO | 2015/012315 A1 | 1/2015 |

OTHER PUBLICATIONS

McGrath et al., Brain Res. Bull., 83:207-213 (2010) (Year: 2010).*
Zheng et al., Biomed. Microdevices, 13(1):1-22 (2011) (Year: 2011).*
International Preliminary Report on Patentability and Written Opinion issued in corresponding International Patent Application No. PCT/JP2015/080588 dated May 11, 2017.
International Search Report issued in corresponding International Patent Application No. PCT/JP2015/080588 dated Jan. 19, 2016.

* cited by examiner

CELL ISOLATION METHOD AND CELL TRAPPING FILTER

TECHNICAL FIELD

The present invention relates to a cell isolation method and a cell trapping filter used for the cell isolation method.

BACKGROUND ART

Since cancer is ranked high in causes of death in various countries around the world, early detection and treatment of cancer is desired. Most of death of human beings by cancer is caused by a metastasis and recurrence. A metastasis and recurrence of cancer occur when a cancer cell is fixed on and invade a vessel wall of a tissue of another organ from primary lesion via a blood vessel or a lymph vessel, and form a micrometastasis. Such a cancer cell circulating in the human body via a blood vessel or a lymph vessel is called circulating cancer cells (Circulating Tumor Cells, hereinafter referred to as "CTC" in some cases).

If the presence or absence and the amount of cancer cells in the blood vessel (CTC) which can cause a metastasis and recurrence of cancer can is enabled, great contribution to cancer treatment becomes possible. As a conventional technique for trapping cancer cells in the blood, for example, the constitution described in Patent Literature 1 is known. The technique described in Patent Literature 1 captures cancer cells in the blood by a filter, and the literature shows a manufacturing method using semiconductor technology of the filter, the shape of a cell unit in which the filter is stored, and the structure of a flow pass to let the blood and a treatment liquid flow.

CITATION LIST

Patent Literature

Patent Literature 1: Publication of US Patent Application No. 2011/0053152

SUMMARY OF INVENTION

Technical Problem

Recent years, however, there are demands for observation of each individual cancer cell for the purpose of more accurately grasping the situation of cancer cells in the blood. However, even if cancer cells are trapped on a filter, for example, using the technique described in Patent Literature 1, it is difficult to observe individual cancer cells. In addition, while it is difficult to handle cancer cells on a filter due to a tendency for cancer cells on a filter to elastic deformation, observation of damaged cancer cells cannot be suitably carried out.

The present invention was made taking the above into account, and an object of the present invention is to provide a cell isolation method which can isolate cancer cells trapped on a cell trapping filter without damaging the cancer cells and a cell trapping filter used for the cell isolation method.

Solution to Problem

To achieve the above-mentioned object, a cell isolation method according to one embodiment of the present invention includes: a cell trapping step of allowing a test liquid to pass through a cell trapping filter which has a plurality of through-holes in the thickness direction, thereby trapping isolation target cells contained in the test liquid on one surface of the cell trapping filter; a gel embedding step of introducing a stimulus-responsive hydrogel onto the one surface of the cell trapping filter on which the cells have been trapped in the cell trapping step, thereby embedding the cells in the stimulus-responsive hydrogel; a gel hardening step of applying a stimulus to the stimulus-responsive hydrogel in which the cells are embedded, thereby hardening the stimulus-responsive hydrogel; and a detachment step of detaching the stimulus-responsive hydrogel that was hardened in the gel hardening step from the cell trapping filter.

In the above-mentioned cell isolation method, a stimulus-responsive hydrogel is introduced onto the one surface of the cell trapping filter 2 on which the cells have been trapped in the cell trapping step, thereby embedding the cells in the stimulus-responsive hydrogel; thereafter a stimulus is applied to the stimulus-responsive hydrogel, thereby hardening the stimulus-responsive hydrogel; and the stimulus-responsive hydrogel that was hardened is detached from the cell trapping filter. In this way, since the cells are handled in a state where the cells are embedded in the stimulus-responsive hydrogel by isolating the cells using the stimulus-responsive hydrogel, the handling property is improved as compared with that in a case where isolation target cells are directly handled, and it is enabled to isolate the cells without damaging the cells.

At this point, in the gel hardening step, there can be an aspect wherein only the periphery of the isolation target cells in the stimulus-responsive hydrogel in which the cells are embedded is locally hardened in the gel hardening step.

As described above, in a case of constitution wherein only the periphery of the isolation target cells is hardened in the gel hardening step, the handling property is further improved, since hydrogel individually hardened for each cell can be handled.

In addition, the cell trapping filter according to one embodiment of the present invention is a cell trapping filter used for the above-mentioned cell isolation method, characterized in that the distance between the adjacent through-holes on the side of the one surface is 80 µm or more.

Regarding the cell trapping filter 2 used for the above-mentioned cell isolation method, since the cells trapped in the adjacent through-holes can be prevented from being hardened at once due to the constitution where the distance between adjacent through-holes is 80 µm or more on the side of one surface, isolation of cells can be suitably carried out.

Advantageous Effects of Invention

According to the present invention, a cell isolation method which can isolate cells trapped on a cell trapping filter without damaging the cells and a cell trapping filter used for the cell isolation method are provided.

DESCRIPTION OF EMBODIMENTS

The embodiments for carrying out the present invention will be explained hereinafter in reference to the attached drawings. Additionally, same elements are assigned same signs in the description of the drawings, and overlapping explanations are omitted.

Figure 1:
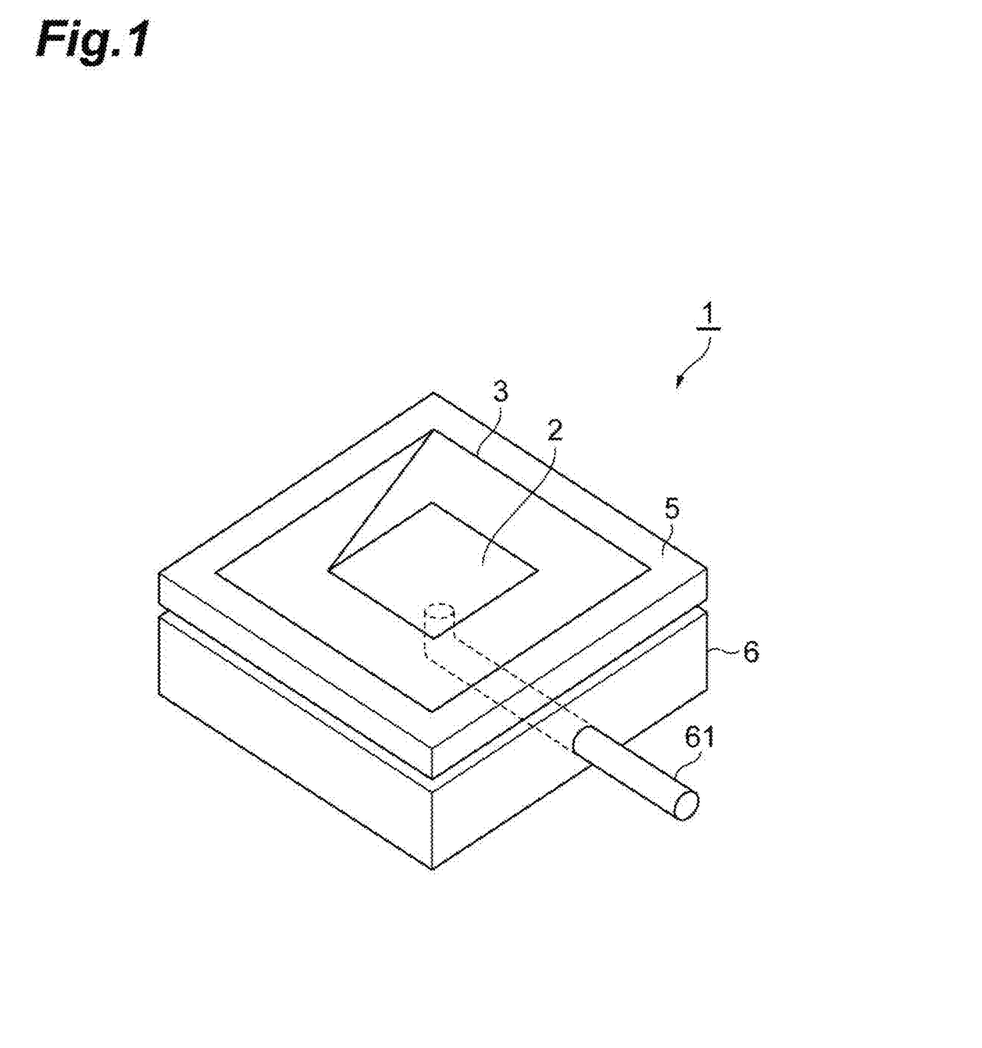
FIG. 1 is a schematic constitution diagram of a cell trapping device.
Figure 2:
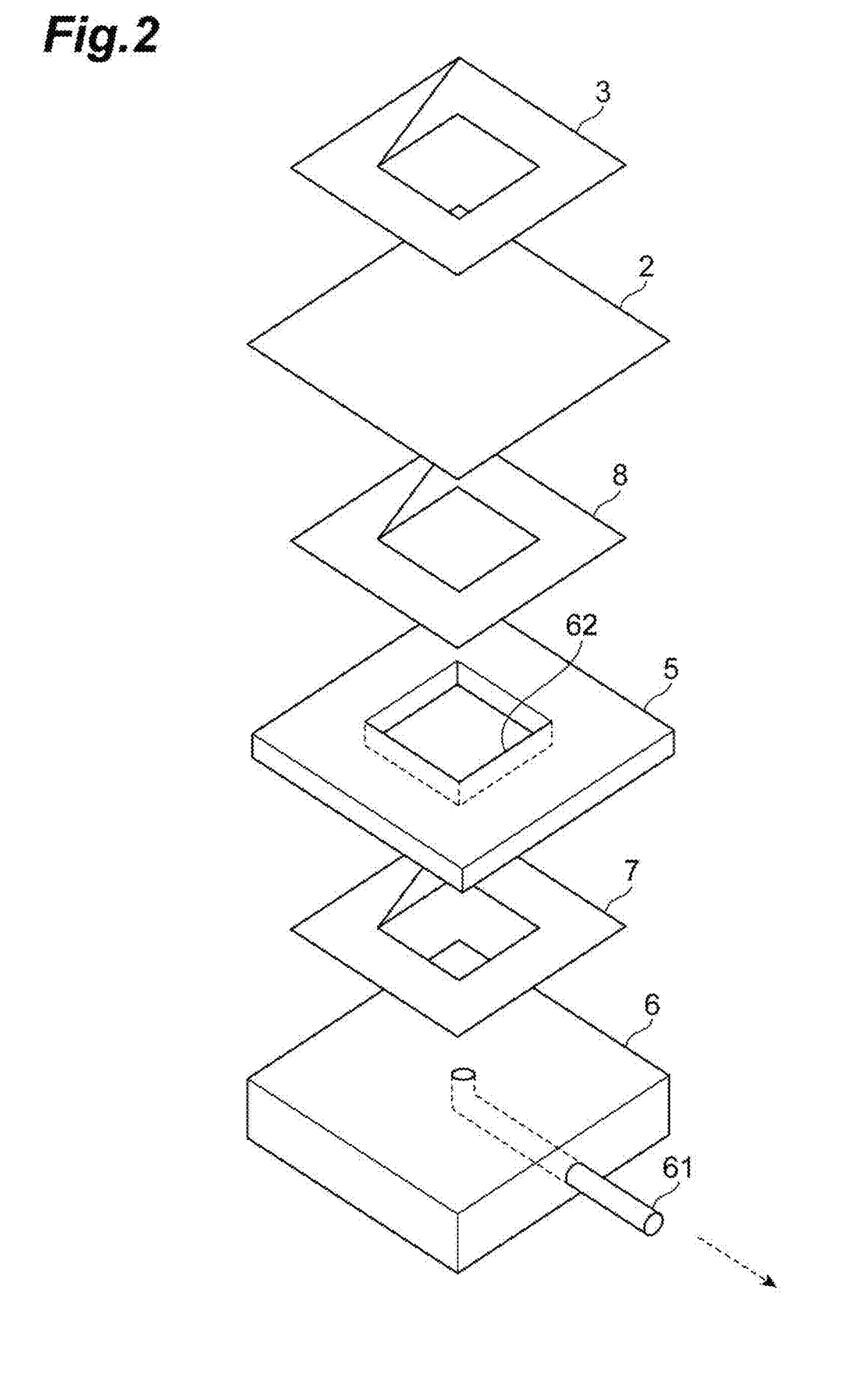
FIG. 2 is an exploded perspective view of a cell trapping device.
Figure 3:
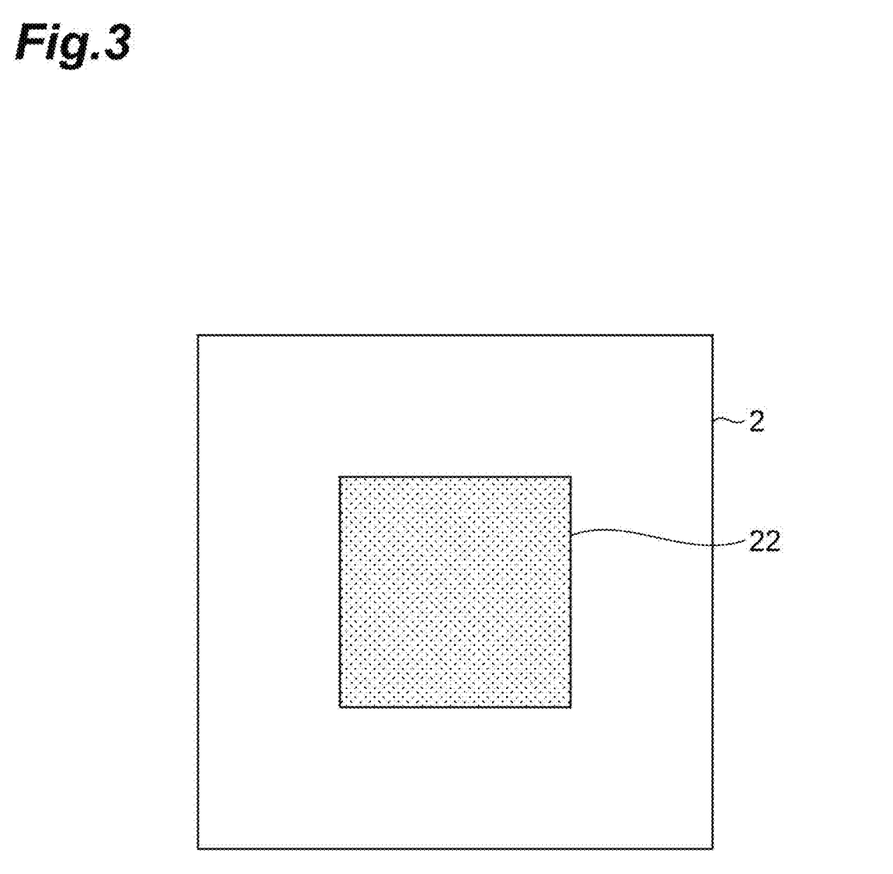
FIG. 3 is a drawing explaining the cell trapping filter.
Figure 4:
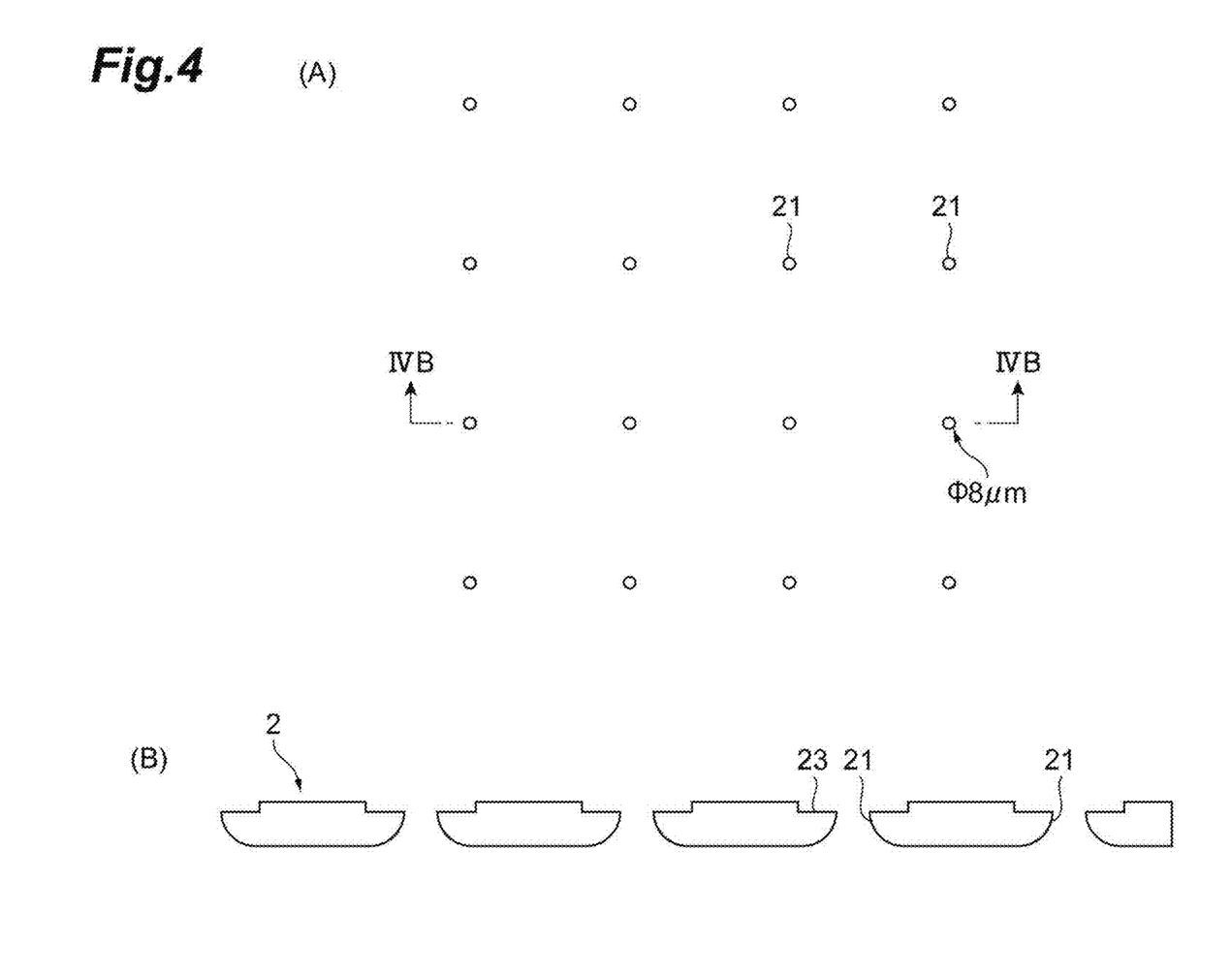
FIGS. 4(A) and 4(B) are drawings explaining the cell trapping filter.

FIG. 1 is a drawing explaining the constitution of a cell trapping device including the cell trapping filter used for the cell isolation method according to one embodiment of the present invention. FIG. 2 is an exploded perspective view of the cell trapping device. In addition, FIG. 3 and FIG. 4 are drawings explaining the cell trapping filter.

The cell trapping device is an apparatus which filtrates a cell dispersion as a test liquid (solution of interest), and thereby traps cells contained in the test liquid. In addition, specification of a cell, counting of the number of cells and the like are carried out by isolating the cells trapped by the cell trapping filter by the isolation method explained in the following embodiments. The cell dispersion as a test liquid includes, for example, blood and a liquid prepared by diluting blood. The cell trapping device is suitably used for the purpose of, for example, trapping rare cells from blood containing rare cells such as circulating cancer cells called CTC, while allowing erythrocytes, platelets and leukocytes contained in the blood (hereinafter generically referred to as "hematocyte components") to pass through the device.

The kind of the rare cells is not limited to CTC. For example, circulating endothelial cells (CEC), and circulating endothelial progenitor cells (CEP) and the like also can be handled as rare cells as a trapping target.

As shown in FIG. 1 and FIG. 2, in the cell trapping device 1, a frame member 3 is provided above the cell trapping filter 2 in which a plurality of through-holes are formed in the thickness direction, and a discharge flow pass is also formed below the cell trapping filter 2.

It is desirable that the quality of the material of the cell trapping filter 2 is as hard as possible, and especially metal is desirable. Since metal has excellent processibility, processing accuracy of the filter can be improved. Thus, the capturing rate of a component as a capturing target can be further improved. In addition, since metal is more rigid than other materials such as plastic, the size and shape are maintained even if force is applied from the outside. Thus, when a component which is a little larger than the through-hole is deformed and allowed to pass through the through-hole, more accurate separation and concentration are enabled.

As the main component of metal, any of nickel, silver, palladium, copper, iridium, ruthenium and chromium, or an alloy thereof is preferable. Among them, it is preferable that especially copper or nickel is used as the main component of metal.

As the cell trapping filter 2, a case where a nickel substrate having a thickness of 25 μm is used will be explained in this embodiment. However, the thickness can be appropriately changed, and, for example, can be 10 μm to 100 μm. As shown in FIG. 3, in the cell trapping filter 2, a filter region 22 in the middle of which a plurality of through-holes 21 are formed is formed.

As shown in FIG. 4(A), the filter region 22 of the cell trapping filter 2 is provided with the plurality of round through-holes 21 having a diameter of 8 μm when viewing from an upper side. The through-holes 21 are arranged in a grid pattern so that the distance between the adjacent through-holes 21 is 125 μm, and 63×63=3969 through-holes 21 are arranged in the filter region 22. In addition, as shown in FIG. 4(B), a concavity 23 having a depth of 2 μm is formed in the periphery of the through-hole 21 on the side of the upper surface (the side from which a test liquid is introduced), when viewing from the section. In addition, the through-hole 21 is slanting so that the hole size becomes gradually larger from the side of the upper surface to the side of the lower surface (the side from which the test liquid is discharged).

The shape and arrangement of the through-holes 21 can be appropriately changed, and it is preferable that the distance between the adjacent through-holes 21 is 80 μm or more in the cell trapping filter 2 according to the present embodiment. By setting the distance between the through-holes 21 in the above-mentioned range, isolation of the trapped cells becomes easier.

Going back to FIG. 1 and FIG. 2, the frame member 3 above the cell trapping filter 2 is provided so that the frame member 3 surrounds the cell trapping filter 2 at the outer side of the filter region 22 of the cell trapping filter 2. The frame member 3 is preferably composed of, for example, a material having an adhesive property to the cell trapping filter 2 such as resin and the like. In addition, a constitution wherein an introducing member and the like having an introducing flow pass is provided above the frame member 3 for introducing a test liquid or a treatment liquid to the cell trapping device 1 is also possible.

Below the cell trapping filter 2, a discharge flow pass 61 for discharging a test liquid which passed through the through-holes 21 of the cell trapping filter 2 from the upper side to the lower side and a discharge region 62 for transferring the test liquid to the discharge flow pass 61 are provided by a frame member 5 and a flow pass member 6.

Concretely, the discharge flow pass 61 is formed in the flow pass member 6. On the upper part of the flow pass member 6, the frame member 5 is provided via a seal member 7. The frame member 5 is a circular member inside which an opening corresponding to the filter region 22 is formed. The region surrounded by the frame member 5 is referred to as the discharge region 62. Between the cell trapping filter 2 and the frame member 5, a seal member 8 is provided.

The frame member 5 and the flow pass member 6 can be composed of resin and the like. The frame member 5 can be composed of, for example, PMMA (poly(methyl methacrylate)). In addition, the flow pass member 6 can be a constitution formed by forming the discharge flow pass 61 by a silicon tube and covering the periphery with PDMS (poly(dimethylsiloxane)). It is preferable that each of the seal members 7 and 8 is composed of a material having an adhesive property to the cell trapping filter 2, the frame member 5 and the flow pass member 6. In addition, as the frame member 3 and the seal members 7 and 8, for example, in situ PCR seal (manufactured by Bio-Rad Laboratories, Inc.) can be used.

In the cell trapping device 1 thus formed, the discharge flow pass 61 is connected to a pump and the like, and a test liquid and the like is suctioned by suction by the pump, thereby a test liquid passes through the through-holes 21 of the cell trapping filter 2 and cells which cannot pass through the through-holes 21 are trapped on the side of the upper surface of the cell trapping filter 2 at the same time.

Additionally, before introducing the test liquid, the test liquid can be suitably introduced by filling inside of the cell trapping device 1 with, for example, PBS (0.5% BSA (N,O-bis(trimethylsilyl)acetamide), 2 mM EDTA (ethylenediaminetetraacetic acid)) and the like. In addition, even after trapping cells, it is preferable to carry out washing treatment of the trapped cells with PBS and the like. Additionally, regarding the cells after trapping, desired treatment can be carried out using a fixing liquid, a staining liquid and the like. In this case, a method of introducing a fixing liquid, a staining liquid and the like into the cell trapping device 1, allowing the liquid to stand still for a given period of time, and thereafter washing the cells with PBS can be used.

Figure 5:
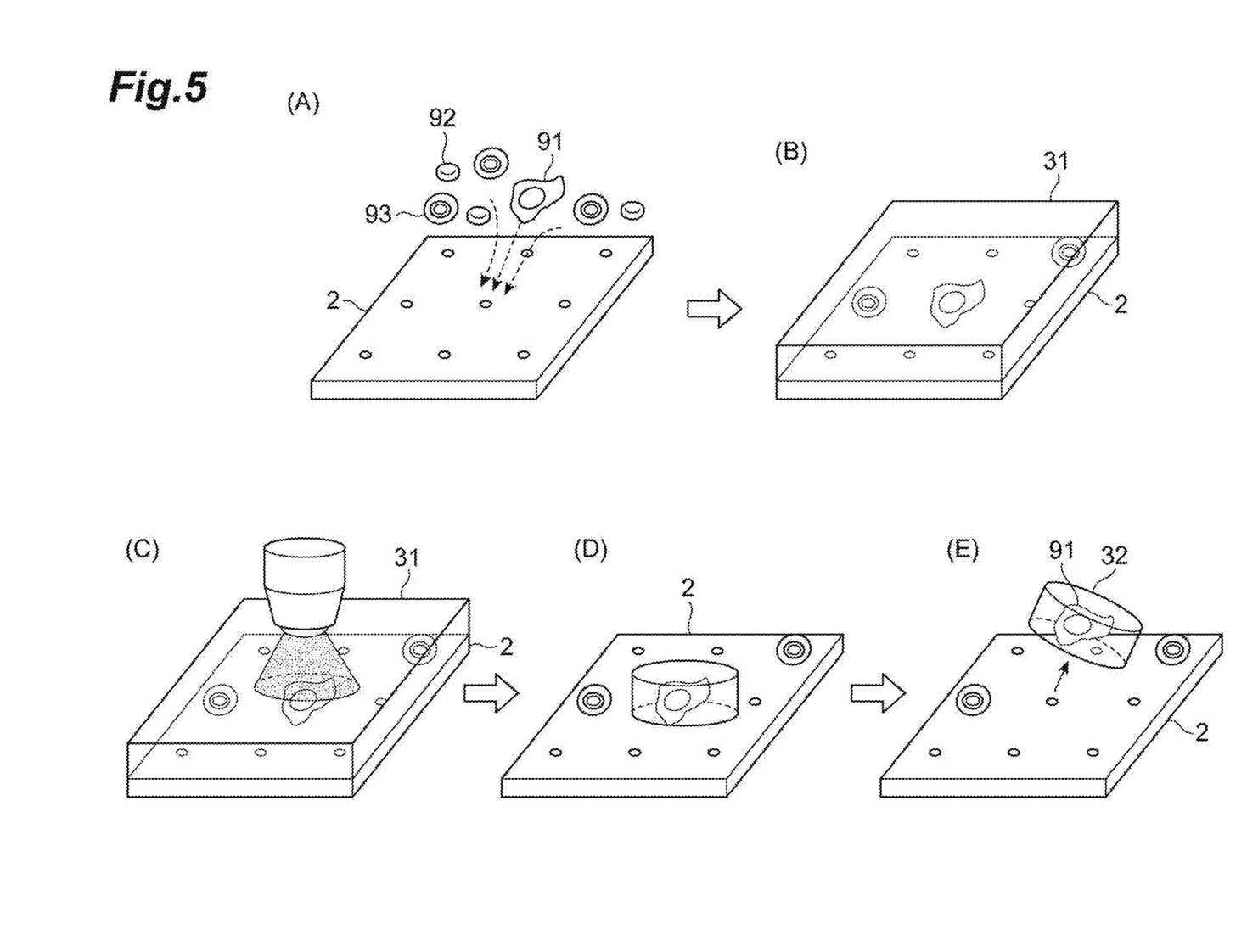
FIGS. 5(A) to 5(E) are drawings explaining the cell isolation method.

Next, the isolation method of cells from the cell trapping device 1 will be explained, while referring to FIGS. 5(A) to 5(E). FIGS. 5(A) to 5(E) are drawings explaining the isolation method of cells using the cell trapping device 1. First, as shown in FIG. 5(A), the test liquid passes through the through-holes 21 of the cell trapping filter 2, and thereby the cells as a trapping target such as CTC are trapped on the through-holes 21 (cell trapping step). On this occasion, other cells such as an erythrocyte 92 and a leukocyte 93, which are blood components, in addition to CTC91 as a trapping target may also be trapped on the cell trapping filter 2.

Next, a stimulus-responsive hydrogel is introduced onto the side of the upper surface of the cell trapping filter 2 on which the cells are trapped, thereby embedding the trapped cells by the stimulus-responsive hydrogel 31 (gel embedding step). The stimulus-responsive hydrogel 31 indicates a hydrogel which responds to slight change in external environments such as temperature, an electric field and light and dramatically changes the physico-chemical properties such as hydrophilic/hydrophobic property. In the cell isolation method according to the present embodiment, a gel which responds to a stimulus and is hardened is suitably used.

Figure 6:
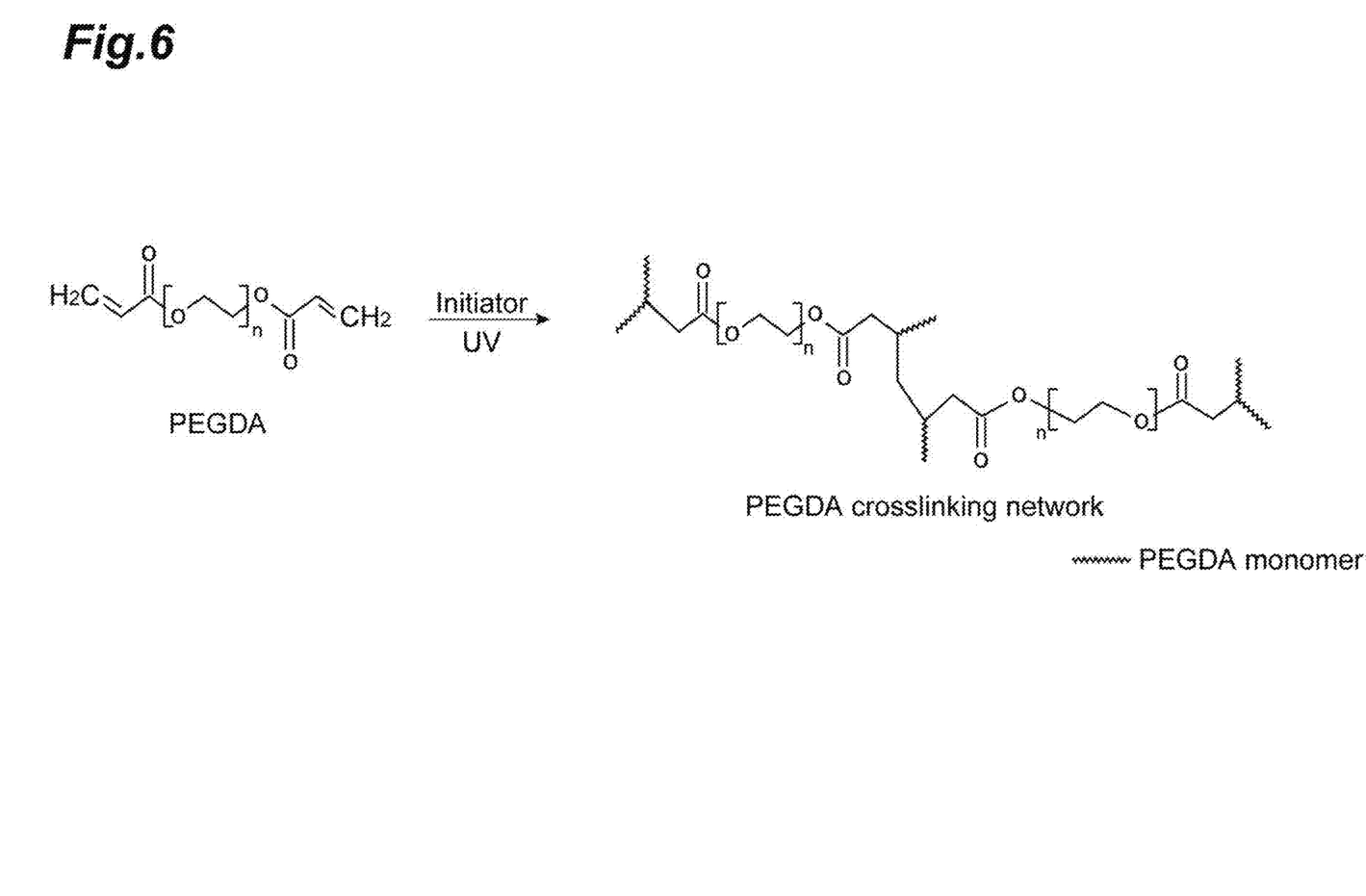
FIG. 6 is a drawing explaining PEGDA.

As such a stimulus-responsive hydrogel, for example, polyethyleneglycol diacrylate (PEGDA) can be used. PEGDA can obtain a cross-linked structure by ultraviolet irradiation, as shown in FIG. 6. In addition, other stimulus-responsive hydrogels include poly(N-isopropylacrylamide) (PNIPAAm), chitosan gel and the like.

When PEGDA is used, for example, a method of introducing a liquid to which 2-hydroxy-2-methylpropiophenone is added onto the cell trapping filter 2 and laminating a cover glass on the frame member 3 can be used.

When PEGDA is used, the amount of the stimulus-responsive hydrogel to be introduced is not specifically limited, so long as the amount is an amount which can embed the isolation target cell. For example, it is preferable that the stimulus-responsive hydrogel is introduced so that the height of the stimulus-responsive hydrogel introduced onto the cell trapping filter 2 is about 100 μm to 600 μm. By setting such a range, the isolation target cells having a size of about 10 μm to several tens of micrometers can be suitably embedded. In addition, the handling property of the hydrogel after hardening is improved. When the height is 100 μm or lower, handling of the hydrogel after hardening is difficult. In addition, when the height is higher than 600 μm, there is a possibility that it is difficult to suitably control the size of the region to be hardened. It is regarded that the amount of the stimulus-responsive hydrogel to be introduced is more preferably about 200 μm to 300 μm.

Next, as shown in FIG. 5(C) and FIG. 5(D), the stimulus-responsive hydrogel 31 is hardened (gel hardening step). When the stimulus-responsive hydrogel 31 is photocurable, light from a light source is irradiated only to the periphery of the cells as a trapping target, and thereby only the periphery of the cells can be hardened. Additionally, when PEGDA is used as the stimulus-responsive hydrogel 31, ultraviolet laser light is irradiated, and thereby PEGDA in the periphery of the cells can be hardened. By selectively hardening the stimulus-responsive hydrogel in the periphery of the cells, the cells can be hardened separately from other cells.

Thereafter, as shown in FIG. 5(E), the stimulus-responsive hydrogel 32 after hardening is detached from the cell trapping filter 2 (detachment step). Thus, the isolation target cells (CTC91) can be individually taken out. After detachment, the cells can be individually taken out from the hydrogel, or used as it is for analysis.

At this point, regarding the case where PEGDA is used as the stimulus-responsive hydrogel, results of detailed examination will be shown.

As the cell trapping filter 2, a Ni substrate in which through-holes 21 having a diameter of 8 μm are arranged at a distance of 125 μm in a grid pattern was prepared. In addition, as the cells as a trapping target, 100 or 1000 cells of NCI-H1975 cells or HCC827 cells were added to 1 ml of blood of a healthy person and PBS (0.5% BSA, 2 mM EDTA) and used as a test liquid.

First, 1 ml of PBS was introduced to the cell trapping device 1, and inside of the cell trapping device 1 was filled with PBS. Next, the test liquid was introduced into the cell trapping device 1, and the liquid was delivered at a flow rate of 150 to 1750 μl/min using a peristaltic pump. Thereafter, in order to let the hematocyte components in the test liquid thoroughly flow, 1 ml of PBS was introduced to carry out washing, and suction operation was carried out for the liquid by the peristaltic pump. Thus, PBS in the cell trapping device 1 was removed, and the cells were trapped on the through-holes 21 of the cell trapping filter 2 at the same time. Thereafter, the flow rate was changed to 200 μm/min, and 4% paraformaldehyde (PFA) in PBS was introduced thereto, and allowed to stand still for 15 minutes as cell fixation treatment. PFA in PBS in the cell trapping device 1 was washed with PBS, substituted with 0.2% TritonX-100 in PBS, and allowed to stand still for 15 minutes, to carry out permeabilization treatment. Next, after washing with PBS, PBS was substituted with a staining liquid (FITC-labeled anti-cytokeratin antibody, PE-labeled anti-CD45 antibody, Hoechst 33342) and allowed to stand still for 30 minutes, to carry out staining Thereafter, the cells were washed with PBS.

Thereafter, a liquid wherein 2-hydroxy-2-methylpropiophenone was added to PEGDA of Mn 250, 575, 700 at a ratio of 1.0% was prepared, and introduced onto the cell trapping filter 2 of the cell trapping device 1, and a cover glass was laminated on the upper surface thereof. Thereafter, the cell trapping device 1 was placed on a confocal laser scanning microscope (FV1000-D IX81; manufactured by Olympus Corporation), and isolation target cells on the substrate were selected using a 10× objective lens. After changing the objective lens to a 100× oil immersion lens, the lens was allowed to contact with the cover glass, and exciting light of which laser intensity was 1.4 mW and of which wave length was 405 nm was irradiated for 180 seconds, to locally harden PEGDA. Thereafter, the cover glass was detached, and hardened hydrogel was detached from the cell trapping filter 2, thereby the cells embedded in the hydrogel could be isolated.

Figure 7:
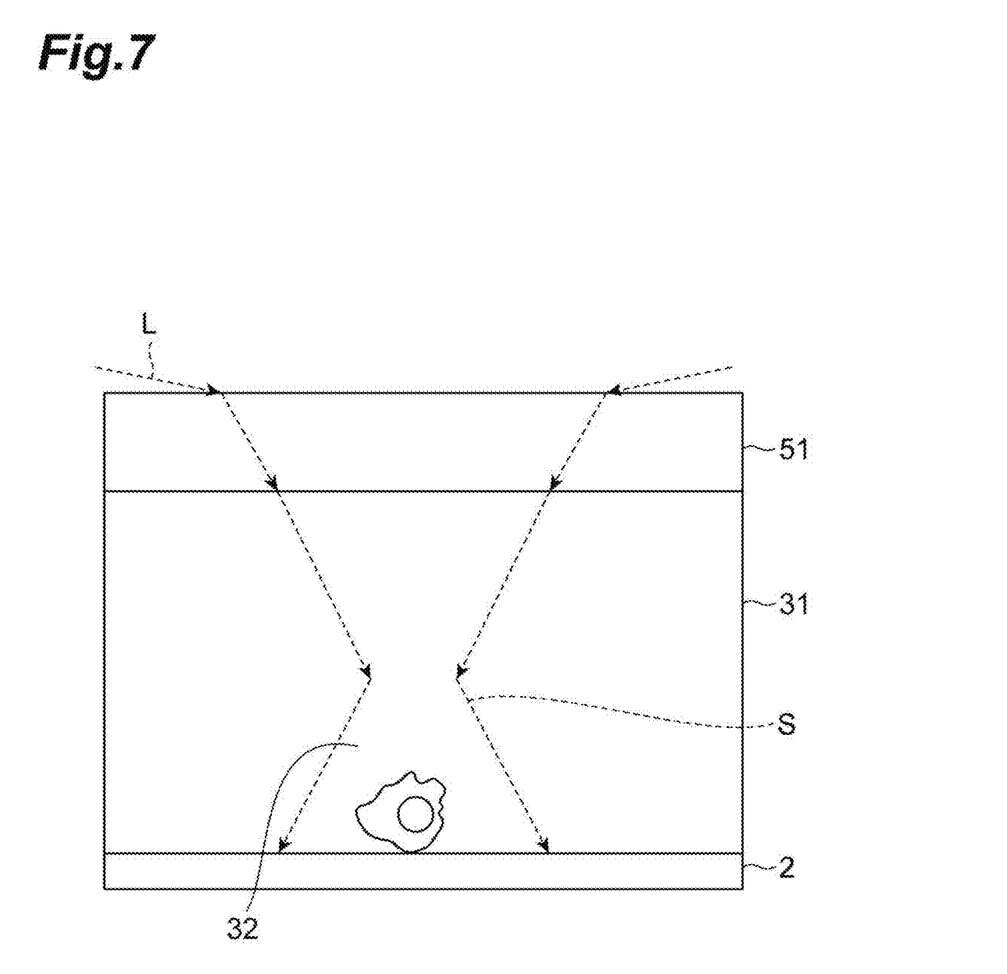
FIG. 7 is a drawing explaining the structure of PEGDA after hardening.
Figure 8:
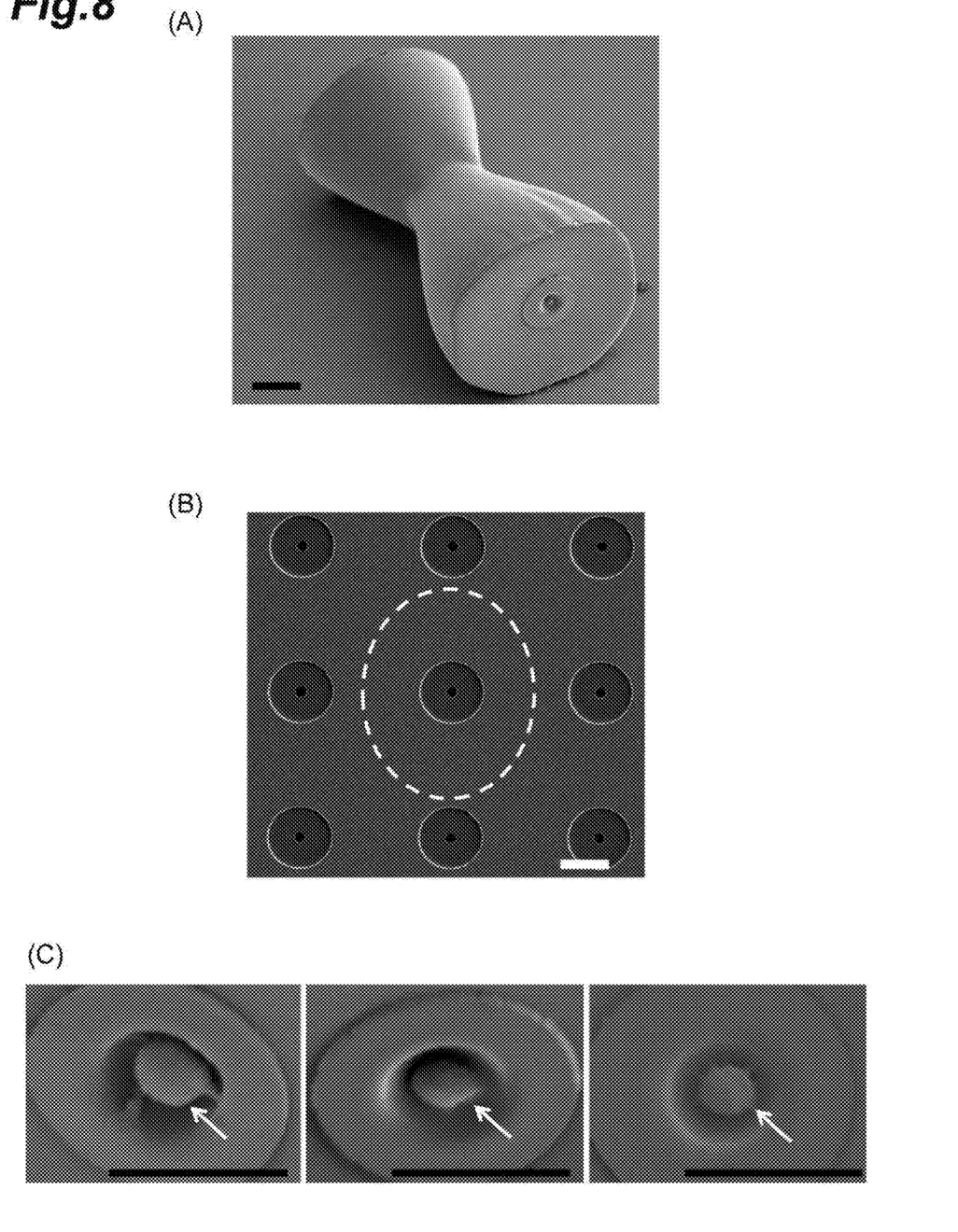
FIGS. 8(A) to 8(C) are SEM images of PEGDA after isolation.

The shape of hydrogel 32 which is hardened by light after covered with a cover glass 51 on the cell trapping filter 2 is schematically shown in FIG. 7. In the hydrogel 31, the region surrounded by rays of light L indicated by broken lines is hardened. In addition, the results of photography of the detached hydrogel (PEGDA) by a scanning electron microscope (SEM) are shown in FIGS. 8(A) to 8(C). FIG. 8(A) is a whole image of the detached hydrogel. In addition, FIG. 8(B) is an image wherein the region where the detached hydrogel existed is indicated by a broken line. In addition, FIG. 8(C) is an enlarged image of the hydrogel corresponding to the periphery of the through-hole 21 of the cell trapping filter 2, and shows that a cell is trapped.

The size of the hydrogel 32 after hardening is about 100 μm to 400 μm in width (the size at the surface opposite to the cell trapping filter 2) and about 100 μm to 500 μm in height. In addition, when laser light is irradiated to PEGDA, the hydrogel after hardening has a shape wherein the central part has a line symmetry narrow part, as shown in FIG. 7. At this time, the narrow part S (see FIG. 7) is thought to be a focal plane of the objective lens. Additionally, the shape of the hydrogel such as presence or absence of the narrow part S is changed by laser irradiation conditions or the height of the hydrogel, and the like. When the hydrogel after hardening has a narrow part S, it is easier to hold the hydrogel by tweezers and the like, and thereby the handling property is improved. In addition, since the hydrogel in which the cell is embedded is sufficiently larger as compared with a cell alone, visual recognition with the naked eye is also possible. Therefore, as compared with a case where a cell alone is handled, the handling property is further improved.

When the height of the hydrogel (PEGDA) after hardening is 200 μm to 300 μm, the hardened region by laser light could have a diameter of 250 μm or less in the surface on the side opposite to the cell trapping filter 2 (the surface on the side where an isolation target cell existed). If the area of the hardened region can be small, isolation accuracy of the cell can be improved. Thus, it is preferable that the height of PEGDA is 200 μm to 300 μm. On the other hand, when the purpose is to detach a plurality of cells from the cell trapping filter 2 while maintaining the positional relation of the cells, conditions such as the height of PEGDA can be appropriately changed.

Additionally, regarding the cells isolated using PEGDA as described above, amplification reaction of whole genome was carried out. As a result, it was confirmed that the gene dosage is amplified about 450,000- to 530,000-fold as with the case where cells were isolated without using PEGDA. That is to say, inhibition of genome amplification by the hydrogel of PEGDA was not confirmed. Additionally, when a cell is completely embedded by a hydrogel of PEGDA, since an enzyme and the like involved in amplification of whole genome could not approach the cell, it was confirmed that amplification of the genome dosage did not occur. Thus, if a part of a cell is exposed to outside, amplification of whole genome is possible. Therefore, it is possible to carry out analysis related to the isolated cell (analysis of gene mutation and the like) and the like.

As described above, in the above-mentioned cell isolation method, a stimulus-responsive hydrogel is introduced onto the one surface of the cell trapping filter 2 on which the cells have been trapped in the cell trapping step, thereby embedding the cells in the stimulus-responsive hydrogel; thereafter a stimulus is applied to the stimulus-responsive hydrogel, thereby hardening the stimulus-responsive hydrogel; and the stimulus-responsive hydrogel that was hardened is detached from the cell trapping filter. In this way, since the cells are handled in a state where the cells are embedded in the stimulus-responsive hydrogel by isolating the cells using the stimulus-responsive hydrogel, the handling property is improved as compared with that in a case where isolation target cells are directly handled, and it is enabled to isolate the cells without damaging the cells.

Especially, in a case of constitution wherein only the periphery of the isolation target cells in the stimulus-responsive hydrogel in which the cells are embedded is hardened in the gel hardening step, the handling property is further improved, since hydrogel individually hardened for each cell can be handled.

In addition, regarding the cell trapping filter 2 used for the above-mentioned cell isolation method, since the cells trapped in the adjacent through-holes can be prevented from being hardened at once due to the constitution where the distance between adjacent through-holes 21 is 80 μm or more on the side of one surface, isolation of cells can be suitably carried out. Conventionally, the distance between through-holes was about 60 μm, in order to improve the speed of cell trapping. In this case, although trapping itself of cells is suitably carried out, it is difficult to individually harden a hydrogel in each through-hole. Thus, it was difficult to isolate cells one by one using a hydrogel. In contrast, isolation of each cell using a hydrogel can be suitably carried out by increasing the distance between through-holes 21 in the cell trapping filter 2. Additionally, when a hydrogel may be hardened and taken out in a state where the hydrogel contains a plurality of cells, the distance between the through-holes 21 may be smaller than 80 μm. Even in this case, isolation of cells after trapping can be suitably carried out by using a hydrogel.

Although the cell isolation method and the cell trapping filter according to the present embodiment were explained above, the cell isolation method and the cell trapping filter according to the present invention are not limited to the above-mentioned embodiment, and can be variously changed.

For example, the cell trapping device for which the cell trapping filter is used is not limited to the structure of the above-mentioned embodiment, and can be appropriately changed. So long as the isolation target cell can be trapped in the through-hole 21 of the cell trapping filter 2, the shape and the like thereof are not limited. In addition, the shape and the like of the through-hole 21 of the cell trapping filter 2 are not limited, and the shape of the opening can be exemplified by an oval, a square, a rectangle, a rectangle with rounded corners, a polygon and the like. Additionally, in the point of view of the efficiency of cell trapping, a circle, a rectangle or a rectangle with rounded corners is preferable. A rectangle with rounded corners is a shape consisting of two long sides having equal length and two semicircles.

REFERENCE SIGNS LIST

1 . . . Cell trapping device, 2 . . . cell trapping filter, 3, 5 . . . Frame member, 6 . . . Flow pass member, 7, 8 . . . Seal member, 61 . . . Discharge flow pass, 62 . . . Discharge region.

The invention claimed is:

1. A cell isolation method comprising:
   a cell trapping step of allowing a test liquid to pass through a cell trapping filter which has a plurality of through-holes in the thickness direction, thereby trapping isolation target cells contained in the test liquid on one surface of the cell trapping filter;

a gel embedding step of introducing a stimulus-responsive hydrogel onto the one surface of the cell trapping filter on which the cells have been trapped in the cell trapping step, thereby embedding the cells in the stimulus-responsive hydrogel;

a gel hardening step of applying a stimulus to the stimulus-responsive hydrogel in which the cells are embedded, thereby hardening the stimulus-responsive hydrogel; and a detachment step of detaching the stimulus-responsive hydrogel that was hardened in the gel hardening step from the cell trapping filter.

2. The cell isolation method according to claim 1, wherein only the periphery of the isolation target cells in the stimulus-responsive hydrogel in which the cells are embedded is locally hardened in the gel hardening step.

3. The method according to claim 1, wherein the distance between the adjacent through-holes on the side of the one surface is 80 μm or more.

4. The method according to claim 2, wherein the distance between the adjacent through-holes on the side of the one surface is 80 μm or more.

5. The cell isolation method according to claim 1, wherein the stimulus-responsive hydrogel comprises a material selected from the group consisting of polyethyleneglycol diacrylate, poly(N-isopropylacrylamide) and chitosan gel.

6. The cell isolation method according to claim 1, wherein the stimulus-responsive hydrogel is photocurable.

7. The cell isolation method according to claim 1, wherein the stimulus used in the gel hardening step is light from a light source.

8. The cell isolation method according to claim 1, wherein the stimulus used in the gel hardening step is ultraviolet laser light.

9. The cell isolation method according to claim 1, wherein a height of the stimulus-responsive hydrogel formed on the cell trapping filter in the gel embedding step is from 100 μm to 600 μm.

10. The cell isolation method according to claim 1, wherein a height of the stimulus-responsive hydrogel introduced formed on the cell trapping filter in the gel embedding step is from 200 μm to 300 μm.

11. The cell isolation method according to claim 1, wherein a width of the stimulus-responsive hydrogel after the gel hardening step is from 100 μm to 400 μm.

12. The cell isolation method according to claim 1, wherein a height of the stimulus-responsive hydrogel after the gel hardening step is from 100 μm to 500 μm.

13. The cell isolation method according to claim 1, wherein a shape of an opening of the through-holed of the cell trapping filter is a round, an oval, a square, a rectangular, a rectangle with rounded corners, or a polygon.

14. The cell isolation method according to claim 1, wherein the stimulus-responsive hydrogel after the gel hardening step has a shape in which a central part of the hydrogel has a line symmetry narrow.

* * * * *